United States Patent [19]

Carver et al.

[11] Patent Number: 5,733,888
[45] Date of Patent: Mar. 31, 1998

[54] INJECTABLE COMPOSITION

[75] Inventors: David Carver, Boulder; Timothy Prout, Erie; Hernita Ewald, Denver, all of Colo.; Robyn Elliott, Lanctwarrin; Paul Handreck, Glen Iriis, both of Australia

[73] Assignee: NaPro BioTherapeutics, Inc., Boulder, Colo.

[21] Appl. No.: 594,478

[22] Filed: Jan. 31, 1996

Related U.S. Application Data

[63] Continuation of Ser. No. 995,501, Dec. 22, 1992, abandoned.

[30] Foreign Application Priority Data

Nov. 27, 1992 [AU] Australia ................................. PL6074

[51] Int. Cl.$^6$ ........................ A01D 43/02; C07D 305/14
[52] U.S. Cl. ............................................................ 514/449
[58] Field of Search ................................................ 514/449

[56] References Cited

U.S. PATENT DOCUMENTS

| | | | |
|---|---|---|---|
| 4,814,470 | 3/1989 | Colin et al. | 514/449 |
| 4,942,184 | 7/1990 | Haugwitz et al. | 514/449 |
| 4,960,790 | 10/1990 | Stella et al. | 519/449 |
| 5,157,049 | 10/1992 | Haugwitz et al. | 514/449 |
| 5,254,580 | 10/1993 | Chen et al. | 514/449 |
| 5,504,102 | 4/1996 | Agharkar et al. | 514/449 |

OTHER PUBLICATIONS

Richheimer, Steven L., David M. Tinnermeier and Daniel W. Timmons (1992) "High–Performance Liquid Chromatographic Assay Of Taxol" Anal. Chem. 64:2323–2326.

Ringel, Israel, Susan Band Horwitz (1987) "Taxol is Converted to 7–Epitaxol, a Biologically Active Isomer, in Cell Culture Medium" Journal of Pharmacology and Experimental Therapeutics 242(1)692–698.

Kingston, David G. I. (1991) "The Chemistry of Taxol" Pharmac. Ther. 52:1–34.

Kingston, David, G. I., Neal F. Magri, Chote Jitrangsri (1986) "Synthesis And Structure–Activity Relationships of Taxol Derivatives As Anticancer Agents" Studies In Organic Chemistry 26:219–235.

Magri, Neal F. and David G.I. Kingston (1986) "Modified Taxols. 2. Oxidation Products of Taxol" Journal of Org. Chem. 51:797–802.

Stability, compatability, and plasticizer extraction of taxol (NSC–125973) injection diluted in infusion solutions and stored in various containers. Reports Taxol, vol. 48, Jul. 1991 by Wanda N. Waugh, Lawrence A. Trissel and Valentino J. Stella.

High–Performance Liquid Chromatographic Assay for Taxol in Human Plasma and Pharmacokinetics in Phase I Trial. Cancer Treatment Reports, vol. 71, No. 1, Jan. 1987 by Stephen M. Longnecker, et al.

*Primary Examiner*—Keith MacMillan
*Attorney, Agent, or Firm*—Saliwanchik, Lloyd & Saliwanchik

[57] ABSTRACT

A pharmaceutical formulation of taxol and polyethoxylated castor oil is disclosed to be relatively acidified to a pH of less than 8.1 and preferably within a pH range of 5 to 7, inclusively, by an acidifying agent. Ethanol is optionally included in the formulation which is adapted for use in a body for the treatment of cancer. A formulation method is disclosed and includes the step of mixing an acid with a carrier material, such as polyethoxylated castor oil, to form a carrier solution after which taxol is added in an amount such that the resulting pH is less than 8.1 and preferably in a pH range of 5 to 7. Ethanol may optionally be slurried with the taxol before mixing with the carrier solution. A variety of acidifying agents, a preferred one being anhydrous citric acid, are described.

44 Claims, No Drawings

INJECTABLE COMPOSITION

This is a continuation of application Ser. No. 07/995,501 filed on 22 Dec. 1992, now abandoned.

This invention relates to a solution of taxol having improved stability.

BACKGROUND OF THE INVENTION

Taxol is a compound extracted from the bark of a western yew, *Taxus brevifolia* and known for its antineoplastic activity. It is described for example in The Merck Index, Eleventh Edition 1989, monograph 9049.

In 1977, taxol was chosen for development as an antineoplastic agent because of its unique mechanism of action and good cytotoxic activity against IP implanted D16 melanoma and the human X-1 mammary tumor xenograft. Taxol is believed to function as a mitotic spindle poison and as a potent inhibitor of cell replication in vitro. Other mitotic spindle points (colchicine and podophyllotoxin) inhibit microtubule assembly. Taxol employs a different mechanism of action since it appears to shift the equilibrium of polymerimization/depolymerization toward polymer assembly and to stabilize microtubules against depolymerization under conditions which would cause rapid disaggregation of microtubules. The interference with the polymerization/depolymerization cycle in cells appears to interfere with both the replication and migration of cells.

After extensive preclinical screening in mouse tumor models, taxol entered clinical trials in 1983. Over the past few years, taxol has demonstrated good response rates in treating both ovarian and breast cancer patients who were not benefiting from vinca alkaloid or cisplatin therapy. It has also shown encouraging results in patients with other types of cancer including lung, melanoma, lymphoma, head and neck.

For further information, reference may be made to the U.S. National Cancer Institute's Clinical Brochure for Taxol, revised July 1991, and papers presented at the Second National Cancer Institute Workshop on Taxol and Taxus held in Alexandria, Va. USA on Sep. 23–24, 1992.

BRIEF DESCRIPTION OF THE INVENTION

It is a disadvantage of the known formulation that the taxol therein degrades, with the result that the shelf life of the formulation is unsatisfactory, and there is therefore a need for a taxol solution of improved stability.

Accordingly, in a general aspect the invention provides a solution containing taxol, cremophor EL™ and ethanol, characterized in that the pH of the solution has been adjusted into the range 1 to 8 by addition of an acid.

Acids in the form of powders, for example citric acid, are preferred over those which contain water, for example sulfuric acid. The most preferred acid for use in accordance with the present invention is citric acid but a wide range of acids may be used including the following:

Citric acid—monohydrous
Citric acid—anhydrous
Citric acid—hydrous
Acetic acid
Formic acid
Ascorbic acid
Aspartic acid
Benzene sulphonic acid
Benzoic acid
Hydrochloric acid
Sulphuric acid
Phosphoric acid
Nitric acid
Tartaric acid
Diatrizoic acid
Glutamic acid
Lactic acid
Maleic acid
Succinic acid

DETAILED DESCRIPTION OF THE INVENTION

Due to its limited solubility in water, Taxol is usually prepared and administered in a vehicle containing cremophor EL™ (a polyethoxylated castor oil which acts as a solubilizer) and ethanol. A commercially available solution supplied by Bristol-Myers Squibb (BMS) is formulated with these components and has a pH of 9.1.

As indicated above, the invention essentially teaches addition of an acid to a taxol formulation to adjust its pH into the range 1 to 8, preferable 5 to 7.

In a preferred procedure adopted by the applicant, which it will be clearly understood is non-limiting, the following steps were carried out:

MIXING INSTRUCTIONS

Solution 1

Citric acid was dissolved in absolute alcohol, using a ratio of 8 mls of absolute alcohol to 1 gram of citric acid, and the solution was stirred for fifteen (15) minutes.

Solution 2

Cremophor EL was weighed out into the main mixing vessel.

Solution 3

Solution 1 was added to solution 2, and the container used for solution 2 was washed with a minimum quantity of absolute alcohol to ensure complete transfer of the citric acid. Solution 3 was mixed and bubbled with nitrogen for at least 15 minutes. The taxol was weighed out and slurried using absolute alcohol, using a ratio of 8 ml of absolute alcohol to 1 gm of taxol. The slurried taxol was added to solution 3 and the slurrying vessel was washed with a minimum quantity of absolute alcohol. Solution 3 was adjusted to 75% of required volume using absolute alcohol, and thoroughly stirred for at least 45 minutes until completely dissolved. Once completely dissolved, the volume was checked and made up as necessary with absolute alcohol and the final solution stirred for 5 minutes.

EXAMPLE 1

A solution was prepared with the following formulation:

| Formulation: (Sample 1) | |
| --- | --- |
| Cremophor EL | 0.5 mL |
| Citric Acid (Anhydrous) | 2.0 mg |
| Taxol | 6.0 mg |
| Absolute Alcohol to | 1.0 mL |

The pH of this solution was determined as 6.1.

The stability of this sample was compared with a sample prepared by the formulation stated in the NCI Taxol Clinical brochure (as follows) which had a pH of 9.1. (Sample 2)

| Sample 2 | per mL |
| --- | --- |
| Taxol | 6 mg |
| Cremophor EL | 0.5 mL |
| Absolute Alcohol | to 1 mL |

The solutions were filled into clear type 1 glass 5 mL vials and sealed with rubber bungs.

The solutions were stored at 40° C. for 7 (seven) days and the stability results are shown in Table 1.

|  | Sample 1 | Sample 2 |
| --- | --- | --- |
| pH | 6.2 | 9.0 |
| Potency | 96.6 | 86.7 |
| Major individual impurity | 0.3% | 5.1% |
| Total impurities | 2.0% | 12.2% |

Clearly Sample 1 showed significantly increased stability over Sample 2.

EXAMPLE 2

A solution was prepared with the following formulation:

| Formulation: (Sample 3) | |
| --- | --- |
| Cremophor EL | 0.5 mL |
| Taxol | 6.0 mg |
| Absolute Ethanol | to 1.0 mL | pH adjusted to 6.6 with 1.0 M Acetic Acid.

The solution was filled into clear type I glass 5 mL vials and sealed with rubber bungs.

The solution was stored at 40° C. for 7 days.

The stability results obtained are compared to those seen with Sample 2.

|  | Sample 3 | Sample 2 |
| --- | --- | --- |
| pH | 6.7 | 9.0 |
| Potency | 97.5 | 86.7 |
| Major individual impurity | 0.3% | 5.1% |
| Total impurities | 2.3% | 12.2% |

Again the significantly superior stability of the formulation according to the invention (Sample 3) is evident.

It will be clearly understood that the invention in its general aspects is not limited to the specific details referred to hereinabove.

We claim:

1. In a pharmaceutical formulation adapted for use in treating cancer comprising taxol and polyethoxylated castor oil, the improvement comprising an acidifying agent added to said pharmaceutical formulation in a proportion such that said composition has a resulting pH less than or equal to 7.0.

2. A method of formulating a taxol solution for injection in which the taxol does not readily degrade, comprising the following steps:
    mixing acid with a carrier material to form a first carrier solution; and
    mixing taxol with the first carrier solution to form a taxol solution whereby the taxol in the taxol solution does not readily degrade.

3. A method according to claim 2 wherein said acid is acetic acid.

4. A method according to claim 2 wherein said acid is citric acid.

5. A method according to claim 2 wherein said carrier material is polyethoxylated castor oil.

6. A method according to claim 2 including the step of slurrying said taxol in alcohol before mixing said taxol with the first carrier solution.

7. A pharmaceutical taxol composition comprising:
    taxol;
    polyethoxylated castor oil; and
    anhydrous citric acid in sufficient amounts to improve the stability of the taxol such that at least 95% of the taxol potency is retained when the composition is stored at 40° C. for 7 days.

8. A pharmaceutical formulation according to claim 1 wherein said composition has a pH of between 5 and 7, inclusively.

9. A pharmaceutical formulation according to claim 1 including ethanol as a constituent thereof.

10. A pharmaceutical formulation according to claim 9 wherein said composition has a pH of between 5 and 7, inclusively.

11. A method according to claim 2 wherein said taxol solution has a pH of between 5 and 7, inclusively.

12. A method for improving the stability of a pharmaceutical taxol solution over an extended period, comprising the steps of:
    providing a formulation comprising taxol, a pharmaceutically-acceptable carrier, and an acidifying agent; and
    storing said formulation in a container for at least 7 days.

13. The method of claim 12, wherein said carrier is polyethoxylated castor oil.

14. The method of claim 13, wherein said formulation is anhydrous.

15. The method of claim 12, wherein said acidifying agent is a mineral acid.

16. The method of claim 12, wherein said acidifying agent is an organic acid.

17. The method of claim 12, wherein said acidifying agent is citric acid.

18. The method of claim 12, wherein said acidifying agent is acetic acid.

19. The method of claim 17, wherein said citric acid is anhydrous.

20. The method of claim 4, wherein said citric acid is anhydrous.

21. The method of claim 2, wherein said taxol solution has an apparent pH of between 5 and 7, inclusively.

22. In an anhydrous pharmaceutical formulation comprising taxol and polyethoxylated castor oil, the improvement comprising an acidifying agent mixed in a proportion such that said pharmaceutical formulation has a resulting pH of about 7 or less.

23. The improved pharmaceutical formulation of claim 22, wherein the apparent pH from about 7 to about 5.

24. The improved pharmaceutical formulation of claim 22, wherein said acidifying agent is a mineral acid.

25. The improved pharmaceutical formulation of claim 22, wherein said acidifying agent is an organic acid.

26. The improved pharmaceutical formulation of claim 22, wherein said acidifying agent is acetic acid.

27. The improved pharmaceutical formulation of claim 22, wherein said acidifying agent is citric acid.

28. The improved pharmaceutical formulation of claim 27, wherein said citric acid is anhydrous.

29. An article of manufacture comprising a container and a pharmaceutical formulation contained therein, said pharmaceutical formulation comprising a pharmaceutically-acceptable carrier, taxol, and an acidifying agent mixed in proportion such that said pharmaceutical formulation has a resulting pH of about 7 or less.

30. The article of manufacture of claim 29 further comprising instructions for administering said pharmaceutical formulation to a patient.

31. The article of manufacture of claim 30, wherein said acidifying agent is a mineral acid.

32. The article of manufacture of claim 30, wherein said acidifying agent is an organic acid.

33. The article of manufacture of claim 30, wherein said acidifying agent is acetic acid.

34. The article of manufacture of claim 30, wherein said acidifying agent is citric acid.

35. The article of manufacture of claim 34, wherein said citric acid is anhydrous.

36. The article of manufacture of claim 30, wherein said pharmaceutically-acceptable carrier is polyethoxylated castor oil.

37. The improved pharmaceutical formulation of claim 1, wherein said acidifying agent is a mineral acid.

38. The improved pharmaceutical formulation of claim 1, wherein said acidifying agent is an organic acid.

39. The improved pharmaceutical formulation of claim 1, wherein said acidifying agent is acetic acid.

40. The improved pharmaceutical formulation of claim 1, wherein said acidifying agent is citric acid.

41. The improved pharmaceutic formulation of claim 40, wherein said citric acid is anhydrous.

42. The method of claim 2, wherein said acid is a mineral acid.

43. The method of claim 2, wherein said acid is an organic acid.

44. A pharmaceutical taxol composition comprising:

taxol;

polyethoxylated castor oil; and acetic acid in sufficient amounts to improve the stability of the taxol such that at least 95% of the taxol potency is retained when the composition is stored at 40° C. for 7 days.

* * * * *